United States Patent [19]

Perlin

[11] 4,444,187

[45] Apr. 24, 1984

[54] MINIATURE SURGICAL CLIP FOR CLAMPING SMALL BLOOD VESSELS IN BRAIN SURGERY AND THE LIKE

[75] Inventor: Alfred R. Perlin, Highland Park, Ill.

[73] Assignee: Metatech Corporation, Northbrook, Ill.

[21] Appl. No.: 448,177

[22] Filed: Dec. 9, 1982

[51] Int. Cl.³ .................. A61B 17/00; A61B 17/12
[52] U.S. Cl. .................................. 128/346; 128/325; 128/326
[58] Field of Search ............... 128/346, 354, 325, 326, 128/334 R, 335

[56] References Cited

U.S. PATENT DOCUMENTS

| | | | |
|---|---|---|---|
| 480,165 | 8/1892 | Bates | 128/346 |
| 1,560,687 | 11/1925 | Hauber | 128/346 |
| 1,741,457 | 12/1929 | Glass | 128/325 |
| 1,748,227 | 2/1930 | Hyams | 128/346 |
| 2,060,724 | 11/1936 | Carroll | 128/326 |
| 2,382,385 | 8/1945 | Condit | 128/346 |
| 2,544,037 | 3/1951 | Moseley | 128/346 |
| 2,890,519 | 6/1959 | Storz, Jr. | 128/325 |
| 3,166,819 | 1/1965 | Robbins | 128/346 |
| 3,378,010 | 4/1968 | Codling et al. | 128/346 |
| 3,598,125 | 8/1971 | Cogley | 128/346 |
| 3,705,586 | 12/1972 | Sarracino | 128/346 |
| 3,805,792 | 4/1974 | Cogley | 128/346 |
| 3,815,609 | 6/1974 | Chester | 128/354 |
| 3,827,438 | 8/1974 | Kees, Jr. | 128/346 |
| 3,911,926 | 10/1975 | Peters | 128/346 |
| 4,024,868 | 5/1977 | Williams | 128/346 |
| 4,269,190 | 5/1981 | Behney | 128/346 |
| 4,274,415 | 6/1981 | Kanamoto et al. | 128/325 |
| 4,340,061 | 7/1982 | Kees, Jr. et al. | 128/346 |
| 4,360,023 | 11/1982 | Sugita et al. | 128/325 |

FOREIGN PATENT DOCUMENTS 1324556  3/1963  France ........................... 128/346

OTHER PUBLICATIONS

"Skin Clamps in Cosmetic Blepharoplasty" by M. Feldstein, Arch Ophthal-vol. 88, Dec. 1972, pp. 659-661.

Primary Examiner—C. Fred Rosenbaum
Assistant Examiner—C. W. Shedd
Attorney, Agent, or Firm—Leydig, Voit, Osann, Mayer & Holt, Ltd.

[57] ABSTRACT

A miniature surgical clip made of a single continuous length of spring wire for clamping blood vessels in brain surgery and the like. The clip includes a pair of operating members arranged at an acute angle and connected together at a common apex. The operating members are symmetrically formed and have inwardly bent legs which extend mutually inward in overlapping relation to form spaced parallel portions defining between them a lateral guideway. Each of the inwardly bent legs terminates in a 270° exit loop having straight exiting portions which are captive in, and which extend through, the guideway parallel to one another to form cooperating jaws which are straight and parallel. The operating members are outwardly sprung with respect to one another for biasing the jaws resiliently into clamping engagement. In the preferred form of the invention the operating members have respective operating loops which are arranged perpendicularly to the plane of the clip and in axial alignment with one another for engagement by opposed points on a tweezer-type applicator which applies mutually inwardly directed force for temporary spreading the jaws for engagement of a blood vessel between them.

8 Claims, 11 Drawing Figures

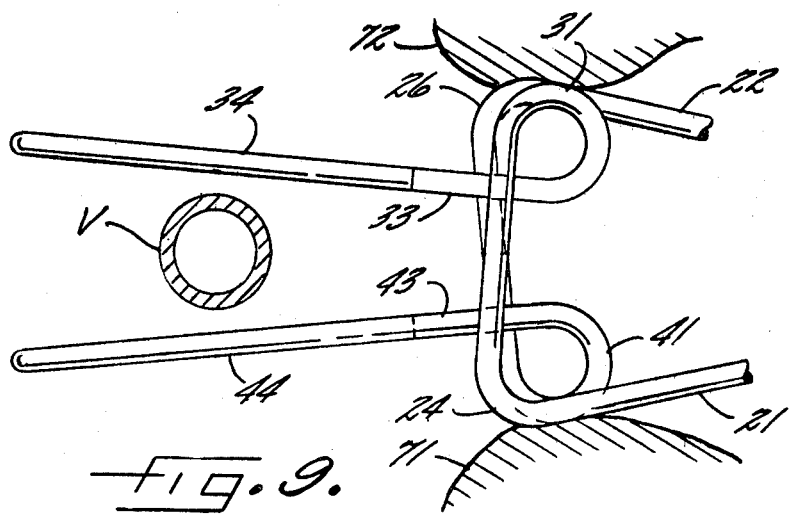
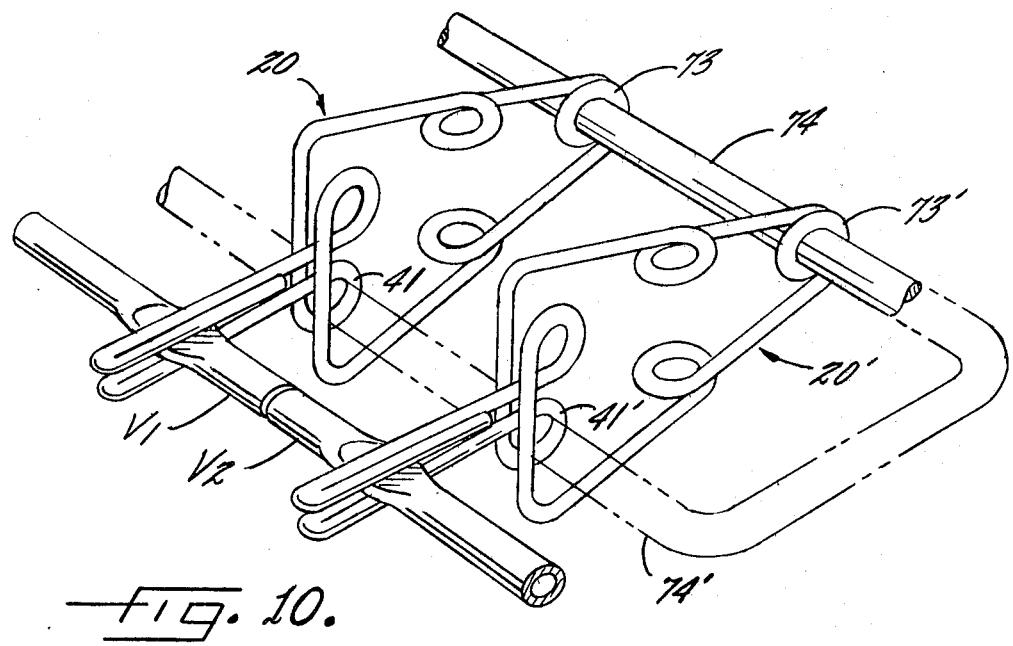
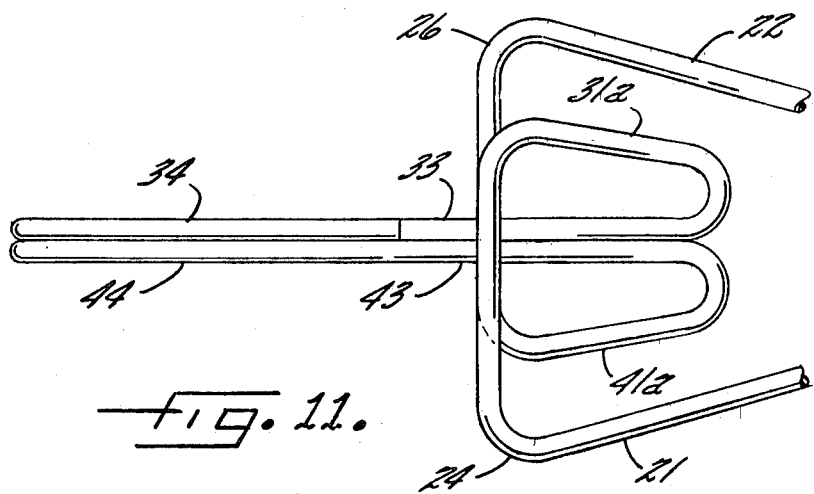

MINIATURE SURGICAL CLIP FOR CLAMPING SMALL BLOOD VESSELS IN BRAIN SURGERY AND THE LIKE

In brain surgery it is frequently necessary to clamp the numerous small blood vessels which tend to bleed profusely, not only to prevent excessive loss of blood by the patient but in order to keep a reasonably clear operating field. In a brain operation, and in correcting the trauma of a head wound, the surgeon must often operate in an extremely small field. When using conventional clamps the field becomes cluttered to the point that the operation is impeded. Moreover, available clamps often crush, cut or otherwise damage the blood vessels which they engage. Conventional designs of clamps are not amenable to reduction in size and level of clamping force; for example, conventional clamps, when reduced in size, become extremely difficult to manipulate.

It is, accordingly, an object of the present invention to provide a miniature surgical clip for clamping blood vessels in brain surgery and the like which may be made in extremely small sizes, down to a few millimeters in maximum dimension, but which is nonetheless, easy to manipulate, that is, apply and remove, either by a mechanical applicator or by the fingertips.

It is another object to provide a surgical clip for a small blood vessels which applies a clamping force which is proportioned to the size of the clip and which is sufficiently low as to prevent inadvertent crushing or other damage to the vessel. It is a related object to provide a surgical clip which may be made in extremely miniaturized form for use with the smallest of blood vessels but which may, nevertheless, be scaled up in size as may be desired for use with blood vessels of larger size and in other parts of the body.

It is an important object of the invention to provide a clip having opposed jaws and which is perfectly reliable in operation with means for maintaining the jaws in precisely opposed relation when the clip is both open and closed.

It is a more specific object to provide a surgical clip which is easily engageable by an applicator of the "tweezer" type, and which permits secure holding by the applicator to prevent inadvertent loss of the clip in the wound. It is, nevertheless, an object of the present invention to provide a clip which is intended to be used with a mechanical applicator but which may be conveniently applied by the fingertips of the surgeon. Regardless of whether the clip is applied by applicator or by fingertip, overstressing of the clip by excessively opening the jaws is avoided thereby protecting the integrity of the clip and preserving the calibration of the clamping force.

It is a general object of the invention to provide a miniature surgical clip made of a single continuous length of spring wire and which cannot, therefore, come apart in the wound as may happen with clips of multi-part construction.

Finally, it is an object of the invention to provide a surgical clip which is of economical construction, which may be easily and quickly made by the bending of wire in a jig on a production line at extremely low cost and which may, therefore, be considered as a disposable item.

Other objects and advantages of the invention will become apparent upon reading the attached detailed description and upon reference to the drawings in which:

FIG. 9 is a fragmentary view similar to FIG. 7 but showing application of force by the fingertips, with the exit loops in bottomed condition to limit the spread of the jaws;

FIG. 10 shows, in side view, two of the clips fitted side by side on a rod to form an "approximator" holding the severed holding ends of a blood vessel adjacent one another for suturing together; and FIG. 11 is a fragmentary view showing an alternate form of clip similar to that shown in FIG. 2 but employing triangularly shaped exit loops.

Figure 1:
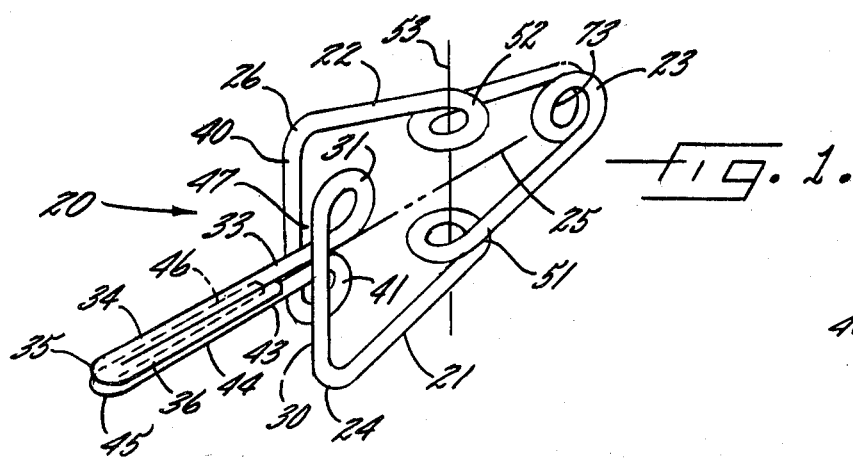
FIG. 1 is an enlarged perspective view of a clip constructed in accordance with the present invention.
Figure 3:
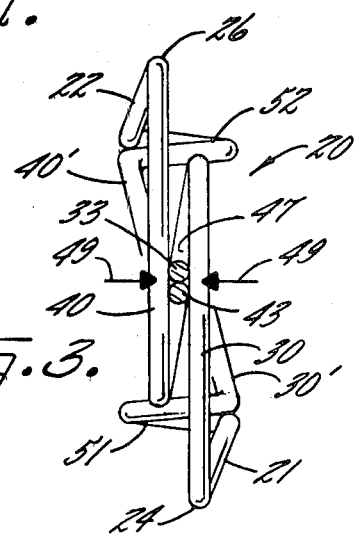
FIG. 3 is an end view looking along the line 3—3 in FIG. 2.
Figure 2:
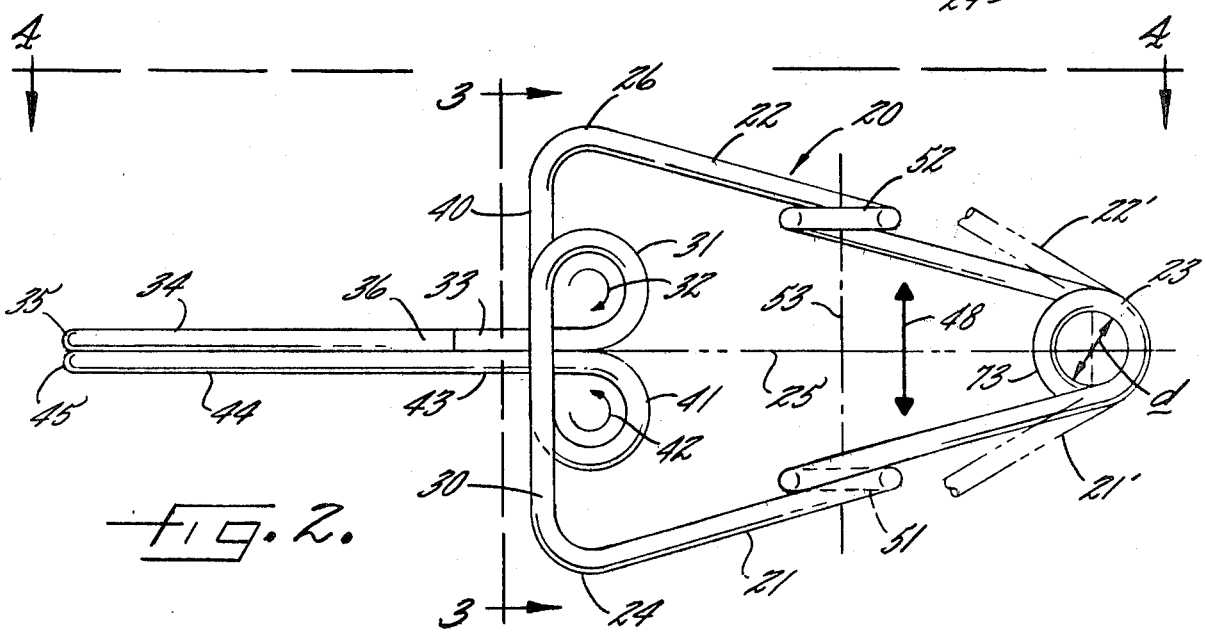
FIG. 2 is a plan view of the clip shown in FIG. 1.
Figure 4:
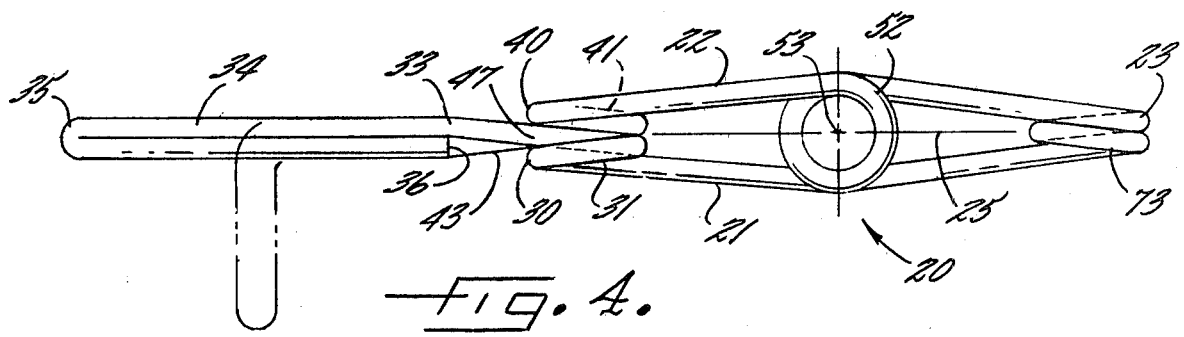
FIG. 4 is a top view looking along line 4—4 in FIG. 2.

Turning now to the drawings and particularly to FIGS. 1-4, there is shown a miniature surgical clip 20 made of a single continuous length of spring wire including a pair of operating members 21, 22 integrally connected at a common apex 23. The portions 21, 22 of the clip are referred to as "operating members" since it is pressure applied mutually inwardly on these members which results in the open and closing movements of the jaws to be described. The members 21, 22 lie adjacent a common plane 25 (FIGS. 3 and 4).

Taking first the operating member 21, it is bent at its lower end 24 to form a base leg 30 having an exit loop 31 which is bent to an angle of 270° as indicated at 32 (FIG. 2), to form a straight exiting portion 33 terminating in a jaw 34 having a tip 35 which is sharply bent upon itself to provide a duck bill jaw element 36.

Similarly, the operating element 22, on the other side of the clip, is bent at 26 to form a base leg 40 terminating an exit loop 41 bent through an angle of 270° as indicated as 42 and having a straight exiting portion 43 leading to a jaw 44 which is, at its tip 45, reversely bent to form a duck bill element 46.

The two base legs 30, 40 extend mutually inwardly in overlapping relation, parallel to one another, to define between them a lateral guideway 47 (see FIG. 3) through which the straight exiting portions 33, 43 of the exiting loops extend and in which they are held captive to maintain the jaws 34, 44 in precise opposition to one another in both the open and closed position of the jaws.

In carrying out the present invention the operating members 21, 22 are pre-stressed outwardly, away from one another, in the direction of the arrows 48, so that the exit loops 31, 41, the exiting portions 33, 43 thereof, and the jaws 34, 44 are all bottomed mutually inwardly upon one another so that the clamp normally occupies its closed position. In other words the members 21, 22 tend to occupy positions 21', 22' (FIG. 2) in the unstressed state. Moreover, in carrying out the invention, the base legs 30, 40 are not bent parallel to the common plane 25 but are bent at symmetrical angles with respect thereto as indicated at 30', 40' (FIG. 3), so that the legs are pre-sprung mutually inwardly with respect to the guideway 47, applying forces 49, 49 which are equal and mutually inward, thereby to maintain the straight exiting portions 33, 43 aligned in a common plane, specifically the plane 25, and so that the jaws 34, 44 are always precisely opposed. The inward bias also insures that the base legs 30, 40 will always be spaced apart by an amount equal to the thickness of the wire of which the device is made.

In accordance with one of the important features of the present invention, each of the operating members 21, 22 has formed at its mid-portion an integral 360° applicator loop perpendicular to the common plane 25, the loops being in substantial axial alignment with one another for engagement by the tweezer type applicator shortly to be described or, alternatively, for engagement by the fingertips of the surgeon where a direct manual application is preferred. Thus, as particularly visible in FIG. 4, the applicator member 21 has a loop 51 formed therein, while the applicator member 22 has an applicator loop 52, the two loops being positioned opposite one another symmetrically with respect to the transverse axis 53, the axis being parallel to the common plane 25.

For the purpose of applying the clip to a blood vessel, an applicator is provided in the form of a clamp having tips terminating in axially opposed sharpened points dimensioned to fit the respective applicator loops for application of a mutually inward force upon the operating members for temporarily spreading the jaws apart for engagement of a blood vessel between them, cooperating stops being provided on the tips of the applicator for limiting the approach of the points to one another, thereby to limit the degree of spread of the jaws to prevent overstressing the clip. Such a clamp, for convenience, is referred to herein as being of the "tweezer" type.

Figure 5:
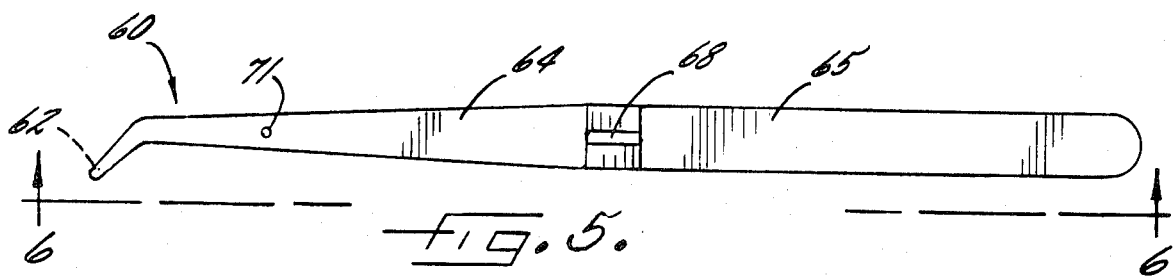
FIG. 5 shows an applicator of the tweezer type usable with the clip of the preceding figures and as viewed, in full size, from the flat side.
Figure 6:
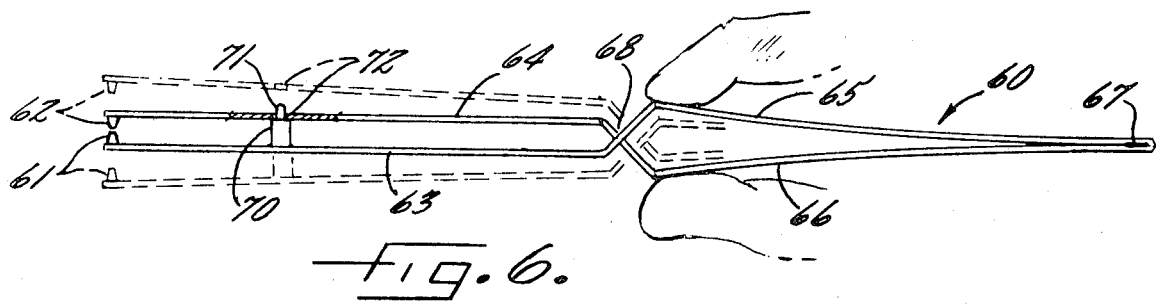
FIG. 6 shows the applicator as viewed edgewise along line 6—6 in FIG. 5.

Referring to FIGS. 5 and 6, the applicator, indicated at 60, has sharpened points 61, 62 which are in opposition to one another and which are respectively mounted upon blades 63, 64 of the tweezer, the blades being connected to pressure pads 65, 66 respectively, which are connected at their base ends to one another at 67, with respect to which they are outwardly sprung, with a "cross-over" at 68 to produce force reversal. A stop 70 (FIG. 6) limits the degree of approach of the points 61, 62. For the purpose of maintaining the points 61, 62 precisely aligned, the blades 63, 64 of the tweezer are fitted with a pilot pin 71 and a pin-receiving opening 72, respectively, with the pin 71 being slightly rounded or pointed at its end to insure entry.

Figure 7:
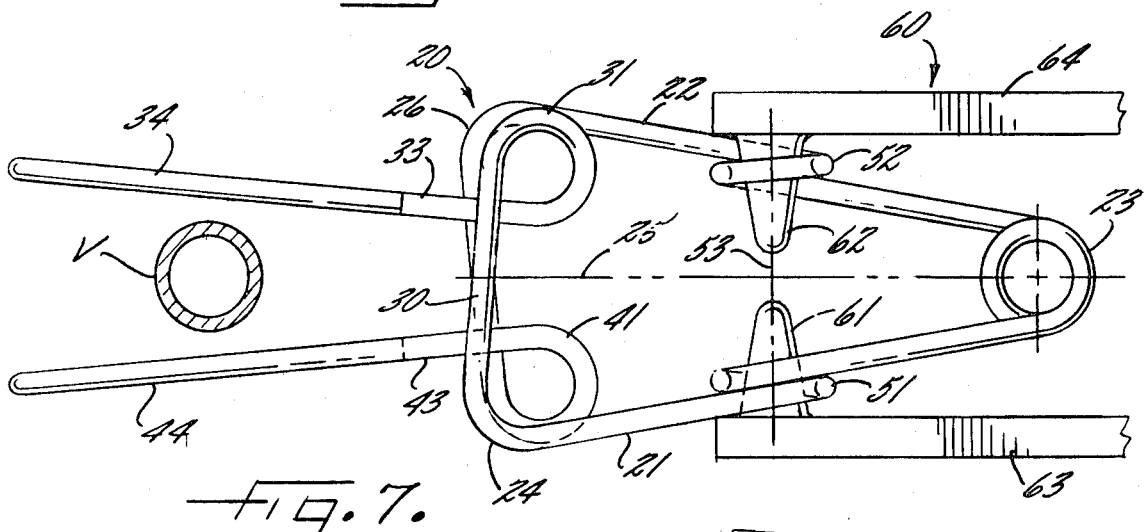
FIG. 7 is a view similar to FIG. 2 but showing the clip engaged by the applicator with the jaws spread apart for engagement of a blood vessel.
Figure 8:
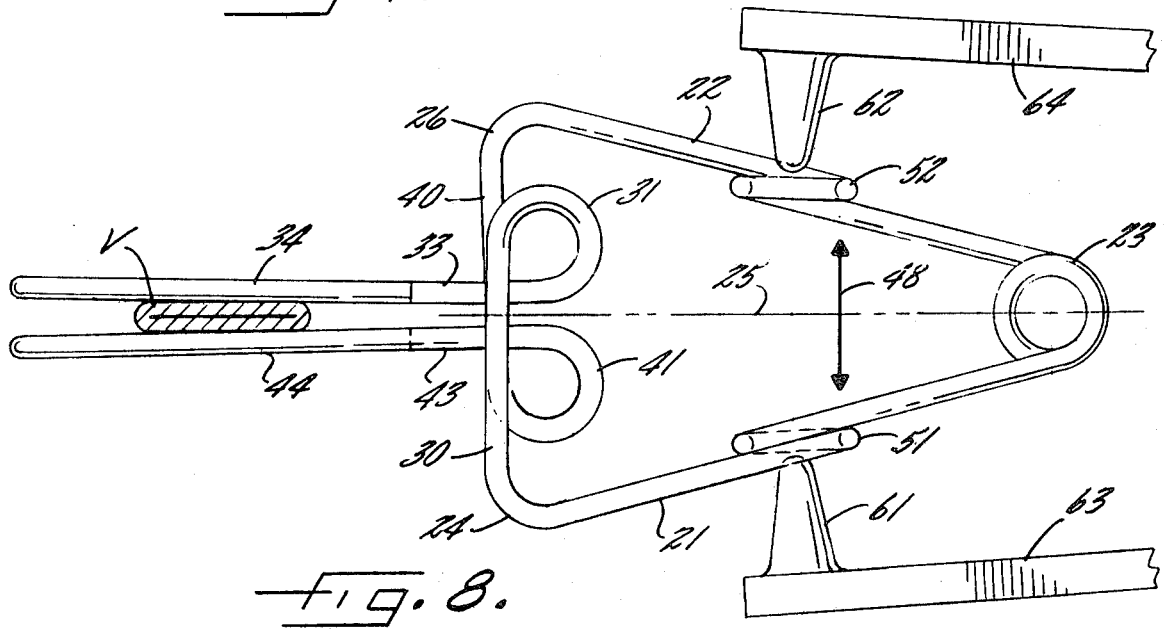
FIG. 8 is a view similar to FIG. 7 but showing the jaws in clamping engagement with the blood vessel.

In use, the tweezer 60 is gripped at the pads 65, 66. Application of manual pressure, to press the pads together (as shown by dotted line in FIG. 6, spreads the points 61, 62 so that they may be engaged with the applicator loops 51, 52 on the clip. Since the pads 65, 66 are outwardly sprung at their point of connection 67, when the manual pressure on the tweezer is released, the points 61, 62 come together, overpowering the clip and spreading the jaws 34, 44 of the clip apart so that the jaws may be placed in straddling relation to a blood vessel V (see FIG. 7). Release of the pressure applied to the pads 65, 66 on the tweezer permits the the points 61, 62 to come together, engaging the applicator loops and spreading the jaws of the clip. Bottoming at the stop 70 limits the degree to which the points 61, 62 can approach one another and therefore limits the amount of spread of the clip jaws to a degree well within the elastic limit of the clip, thus preserving the integrity of the clip and preserving its force calibration. In short, there is assurance that when manual force is reapplied to the pads 65, 66 to spread the points 61, 62 to release the clip, the jaws of the clip will re-close upon the blood vessel with a precisely predetermined force 48 (FIG. 8), thereby avoiding any possibility of crushing or cutting the tender vessel.

It is to be noted that the clip is protected against over stress even when applied directly by the fingertips of the surgeon. Thus as shown in FIG. 9, in which the clip is shown engaged between the thumb and forefinger of the surgeon, indicated at 71, 72, respectively, the bottoming of the exit loops 31, 41 against thumb and forefinger limit the degree of spread. In designing a clip in accordance with the present invention the radius of the exit loops 31, 41 may be tailored to limit the degree of jaw spread to the precise amount which is desired during manual application.

It is one of the features of the present construction that the jaws 34, 44, being constrained in the guideway 47 (FIG. 3), are kept precisely opposed to one another and cannot slip past one another, scissor fashion, which might run the risk of severing the vessel which is intended to be clamped. It is a further feature of the present invention that while clamps of conventional design do not lend themselves well to scaling downwardly in size, the present design of small clip can be scaled upwardly in size for use on larger blood vessels both in the brain and in other parts of the body.

In accordance with one of the features of the present invention, an apex loop in excess of 360° may be formed at the apex 23, permitting at least two of the clips to be strung on a rod which is snuggly fitted in the respective apex loops, the clips being spaced in parallel side-by-side relation for engagement, by their respective jaws, of the opposed ends of a severed blood vessel for holding the ends of the blood vessel in axial alignment as the ends are sutured together. Thus as disclosed in FIGS. 1-4 there is provided, at the apex 23, an apex loop 73 having an inner diameter d. This permits two of the clips to be mounted side-by-side on a rod 74 as shown in FIG. 10, the clips 20 and 20' being rather snugly fitted on the rod so as to hold, conveniently adjacent one another, the severed ends V1, V2 of a blood vessel while the surgeon stitches the ends of the vessel together. If desired the rod may be of "U" shape having a reversely bent portion 74' which is entered in the loops 41, 41' to keep the clips alined, with their jaws in a common plane.

While the exit loops 31, 41 have been described as circular, the exit loops may, if desired, be formed of triangular profile as indicated at 31a, 41a in FIG. 11 with angles substantially matching the triangular profile of the body of the clip itself. This has a number of advantages. The "bottoming" area, which limits the degree of spread, (see FIG. 9) is increased thereby informing the surgeon by touch more promptly and precisely that the bottoming condition has been achieved. Also the length of wire in effective contact in closed position is substantially increased.

The present design provides a high degree of flexibility in the specific design of clips for blood vessels of different size. The size, which may be as small as three to five millimeters in major dimension, provides optimum clamping force on the order of 5 grams for blood vessels of smallest size, with the dimensions being scaled upwardly for vessels of greater size. For each size the amount of clamping force may be preselected based upon the stiffness (spring rate) of the spring wire and the amount of outward pre-stress indicated by the arrows 48 in FIG. 2. If desired the clips may be calibrated in accordance with the degree of clamping force which they exert and segregated accordingly for later use. A calibrating device may be used as disclosed in my prior application Ser. No. 223,210 filed Jan. 8, 1981.

The construction amply meets the objects set forth above: The clip exerts a predetermined safe level of clamping force, may be calibrated in accordance with the clamping force, and retains such calibration, and full structural integrity in spite of repeated usage. The opposed jaws are maintained in direct opposition when the clip is both open and closed. The clip is easily applied by an applicator which is so constructed as to prevent inadvertent loss of the clip in the wound, although the clip may be applied, if desired, by fingertip pressure without affecting its clamping force and with no risk of overstress. The clip is of economical construction, easily and economically formed on a production line basis, and made of a single piece of wire for maximum safety in the wound.

The jaws 34, 44, as illustrated, are both formed of wire reversely bent (at the tips 35, 45) to provide a "full" duckbill to distribute the clamping force. However, if desired, and as apparent to one skilled in the art, only one of the jaws need have the reverse bend; the other may be straight and centered with respect thereto resulting in a "semi" duckbill.

Also while it is preferred to have the jaws lie in the plane of the clip, the jaws may, if desired, be bent so as to extend off to one side as illustrated by the dot-dash line in FIG. 4; indeed the jaws may occupy any angular position between that shown in full lines and that shown in dot-dash. The term "straight" is intended to include jaws which are substantially straight, i.e., having slight curvature.

I claim:

1. A miniature surgical clip made of a single continuous length of spring wire for clamping blood vessels in brain surgery and the like comprising, in combination, a pair of operating members arranged at an acute angle with respect to one another connected together at a common apex and lying adjacent a common plane, the operating members being symmetrically formed and each having an inwardly bent base leg, the inwardly bent legs being extended mutually inwardly in overlapping relation resulting in parallel portions which are spaced apart by an amount equal to the thickness of the wire so as to define between them a lateral guideway lying in the common plane, each of the inwardly bent legs terminating in a 270° exit loop having straight exiting portions which are captive in, and which extend through, the guideway parallel to one another to form cooperating jaws which are straight and parallel, the operating members being outwardly sprung with respect to one another for biasing the jaws resiliently into clamping engagement so that when mutually inward force is applied to the operating members the jaws are spread apart for engagement of a blood vessel between them and so that when the force is released the jaws are guided by the guideway into directly opposed clamping engagement with the blood vessel.

2. A miniature surgical clip made of a single continuous length of spring wire for clamping blood vessels in brain surgery and the like comprising, in combination, a pair of operating members arranged at an acute angle with respect to one another connected together at a common apex and lying adjacent a common plane, the operating members being symmetrically formed and each having an inwardly bent base leg, the inwardly bent legs being extended mutually inwardly in overlapping relation resulting in parallel portions which are spaced apart by an amount equal to the thickness of the wire so as to define between them a lateral guideway lying in the common plane, each of the inwardly bent legs terminating at a 270° exit loop having straight exiting portions which are captive in, and which extend through, the guideway parallel to one another to form cooperating jaws which are straight and parallel, the operating members being outwardly sprung with respect to one another for biasing the jaws resiliently into clamping engagement, each of the operating members having formed at the mid-portion thereof an integral 360° applicator loop perpendicular to the common plane, the applicator loops being in axial alignment.

3. A miniature surgical clip and applicator therefor, the clip being made of a single continuous length of spring wire for clamping blood vessels in brain surgery and the like comprising, in combination, a pair of operating members arranged at an acute angle with respect to one another connected together at a common apex and lying adjacent a common plane, the operating members being formed of substantially straight lengths of wire each having at its central portion a 360° applicator loop perpendicular to the common plane and with the loops in axial alignment with one another, the operating members each having an inwardly bent leg, the inwardly bent legs being extended mutually inwardly in overlapping relation resulting in parallel portions which are spaced apart by an amount equal to the thickness of the wire so as to define between them a lateral guideway lying in the common plane, each of the inwardly bent legs terminating at a 270° exit loop having straight exiting portions which are captive in, and which extend through, the guideway parallel to one another to form cooperating jaws which are straight and parallel, the operating members being outwardly sprung with respect to one another for biasing the jaws resiliently into clamping engagement, and an applicator in the form of a tweezer having tips terminating in axially opposed sharpened points dimensioned to engage the respective applicator loops for application of mutually inward force upon the operating members for temporarily spreading the jaws apart for engagement of a blood vessel between them, and cooperating stops on the tips of the applicator for limiting the approach of the points to one another thereby to limit the degree of spread of the jaws and to prevent overstressing the clip.

4. The combination as claimed in claim 1 or in claim 2 or in claim 3 in which the inwardly bent legs are sprung toward one another in the direction of guideway so that the exiting portions which move in the guideway are forceably constrained into alignment with one another thereby keeping the jaws in alignment in both the open and closed condition.

5. The combination as claimed in claim 1 or in claim 2 in which the exit loops are sufficiently large so that when the operating members are squeezed inwardly by opposed fingertip force resulting in the exit loops moving mutually away from one another, the exit loops move to respective bottoming positions against the fingertips to limit the degree of spread of the jaws and to avoid overstressing the clip.

6. The combination as claimed in claim 1 or in claim 2 or in claim 3 in which the wire forming at least one the jaws is reversely bent upon itself to form a duck bill.

7. The combination as claimed in claim 1 or in claim 2 or in claim 3 in which the operating members form a triangular profile and in which the exit loops are of substantially matching triangular profile.

8. The combination as claimed in claim 1 or in claim 2 or in claim 3 in which an apex loop in excess of 360° is formed at the apex, a rod, at least two of the clips being strung on the rod, the rod being snugly fitted in the respective apex loops, the clips being spaced in parallel side-by-side relation for engagement by their respective jaws of the opposed ends of a severed blood vessel for holding the ends of the blood vessel in axial alignment as the ends are sutured together.

* * * * *